United States Patent [19]

Gehret

[11] Patent Number: 4,582,852
[45] Date of Patent: Apr. 15, 1986

[54] 14- AND 15-HYDROXY MILBEMYCIN DERIVATIVES FOR CONTROLLING PLANT AND ANIMAL PARASITES

[75] Inventor: Jean-Claude Gehret, Aesch, Switzerland

[73] Assignee: Ciba-Geigy Corporation, Ardsley, N.Y.

[21] Appl. No.: 664,677

[22] Filed: Oct. 25, 1984

[30] Foreign Application Priority Data

Nov. 2, 1983 [CH] Switzerland ............. 5909/83
Oct. 2, 1984 [CH] Switzerland ............. 4736/84

[51] Int. Cl.$^4$ ................ C07D 495/20; C07D 495/22; A01N 43/22; A61K 31/365
[52] U.S. Cl. .......................... 514/450; 549/264; 549/265
[58] Field of Search ............ 536/7.1, 6.5; 549/214, 549/264, 265, 266; 514/450

[56] References Cited

U.S. PATENT DOCUMENTS

| | | | |
|---|---|---|---|
| 4,173,571 | 11/1979 | Chabala et al. | 549/264 |
| 4,201,861 | 5/1980 | Mrozik et al. | 536/7.1 |
| 4,289,760 | 9/1981 | Mrozik et al. | 536/7.1 |
| 4,328,335 | 5/1982 | Mrozik | 536/7.1 |
| 4,469,682 | 9/1984 | Mrozik | 549/264 |

FOREIGN PATENT DOCUMENTS 9033288  2/1984  Japan ............................ 549/264

Primary Examiner—Glennon H. Hollrah
Assistant Examiner—Dara L. Dinner
Attorney, Agent, or Firm—Edward McC. Roberts

[57] ABSTRACT

Milbemycin derivatives of the formula I

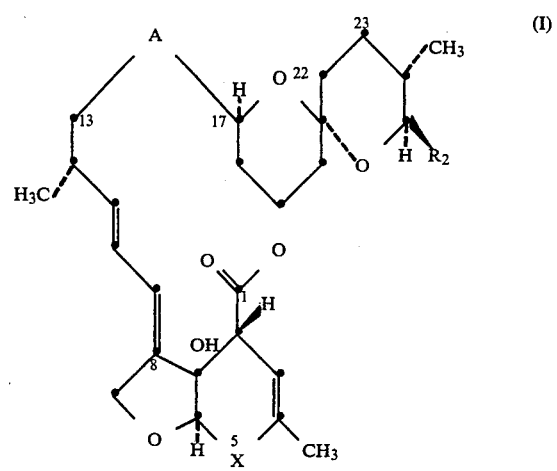

wherein A has the structure

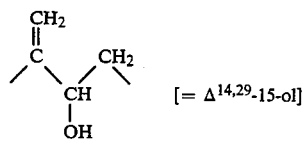

[= $\Delta^{14,29}$-15-ol]

or the structure

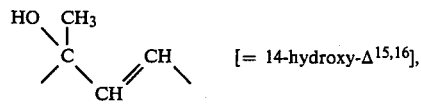

[= 14-hydroxy-$\Delta^{15,16}$],

X is either —CH(OR$_1$)— or —CO—, R$_1$ is hydrogen, a silyl group or an acyl group, and R$_2$ is methyl, ethyl, isopropyl or sec-butyl, can be prepared by singulett oxygen oxidation of the milbemycin derivatives of the formula II herein, wherein X and R$_2$ have the above meanings, and subsequent reduction of the 15- and 14-peroxides obtained as intermediates. Compounds of the formula I can be prepared as such or in the form of compositions for controlling endo- and ectoparasites, in particular nematodes which are parasites of animals.

7 Claims, No Drawings

14- AND 15-HYDROXY MILBEMYCIN DERIVATIVES FOR CONTROLLING PLANT AND ANIMAL PARASITES

The present invention relates to milbemycin derivatives of the formula I, to the preparation thereof by singulett oxygen oxidation, and to the use of said derivatives in pest control by themselves or in suitable formulations.

Compounds of formula I

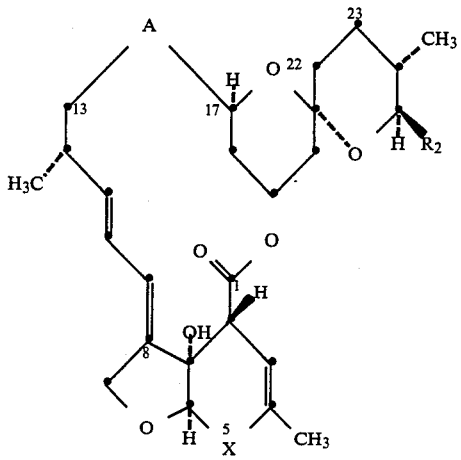

are obtained in two basic structures side by side. In compounds of formula Ia
A is the structure

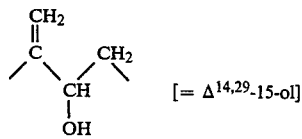

and in compounds of formula Ib
A is the structure

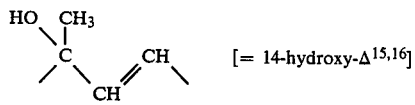

and in both structures X is either

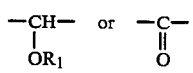

and
$R_1$ is hydrogen or a silyl or acyl group, and
$R_2$ is methyl, ethyl, isopropyl or sec-butyl.

Compounds of the formulae Ia and Ib can be separated by physicochemical methods.

Throughout this specification, compounds wherein $R_2$ is sec-butyl shall also be considered as belonging to the milbemycin derivatives, although strictly they do not come into this category according to conventional classification, but are derived from avermectin derivatives as disclosed in U.S. Pat. No. 4,173,571.

Compounds of formula Ia are preferred within the scope of the present invention and, among these, those compounds wherein X is either —CHOH— or —CO—.

Acyl and silyl groups $R_1$ will in principle be understood as meaning protective groups, the presence of which, however, does not diminish the biological value of the compounds in which $R_1$ is hydrogen.

Suitable acyl groups $R_1$ are $R_3$—CO— and $R_4$—$SO_2$— radicals, in which $R_3$ is preferably an unsubstituted or a halogenated $C_1$-$C_6$ aliphatic radical, or is a phenyl radical which is unsubstituted or substituted by $C_1$-$C_4$ alkyl or halogen, and $R_4$ is a $C_1$-$C_4$ alkyl radical or a phenyl radical which is unsubstituted or substituted by methyl, chlorine or nitro.

Preferred compounds of the formula I are those wherein $R_1$ is hydrogen, a $R_3$—CO— or $R_4$—$SO_2$— radical, in which $R_3$ is a $C_1$-$C_4$ alkyl radical or a phenyl radical which is unsubstituted or substituted by methyl or chlorine, and $R_4$ is methyl, ethyl, phenyl, p-tolyl, o-nitrophenyl or p-chlorophenyl, and $R_2$ is methyl, ethyl, isopropyl or sec-butyl.

Without any restriction being implied, typical examples of substituents $R_3$ are methyl, ethyl, propyl, isopropyl, tert-butyl, phenyl, p-chlorophenyl, and p-tolyl.

Suitable silyl groups are those of the formula

wherein $R_5$ is a $C_1$-$C_4$ aliphatic radical or benzyl, and $R_6$ and $R_7$ are each independently of the other a $C_1$-$C_4$ aliphatic radical, benzyl or phenyl.

An important group of compounds comprises milbemycin derivatives of the formula I, wherein A is as defined for formula I, X is —CHOH— or —CO— and $R_2$ is $isoC_3H_7$.

Another group of preferred compounds of the formula Ia comprises those compounds wherein $R_1$ is the silyl group specified above in which $R_5$ is methyl, ethyl, propyl, isopropyl or tert-butyl, and $R_6$ and $R_7$ are each independently of the other methyl, ethyl, isopropyl, tert-butyl, phenyl or benzyl, and $R_2$ is methyl, ethyl, isopropyl or sec-butyl.

Examples of silyl groups are trimethylsilyl, methyldiphenylsilyl, tri-(tert-butyl)silyl, diphenyl-tert-butylsilyl, bis(isopropyl)methylsilyl and, in particular, tert-butyldimethylsilyl.

The 13-position is unsubstituted in naturally occurring milbemycins ($R_1$=H; $R_2$=$CH_3$, $C_2H_5$ or $isoC_3H_7$). Avermectins, however, carry in the 13-position a β-hydrogen atom and an α-L-oleandrosyl-α-L-oleandrose radical which is linked through oxygen in the α-configuration to the macrolide molecule. Moreover, avermectins differ structurally from the milbemycins in that they contain a 23-OH group or a $\Delta^{22,23}$ double bond and usually a substituent $R_2$=sec-$C_4H_9$. Hydrolysis of the sugar residue of avermectins readily affords the corresponding avermectin aglycones, which carry an allylic 13α-hydroxy group. This OH group can be converted with o-nitrobenzenesulfonyl chloride into a 13β-chloro derivative, the chloro substituent of which can be removed reductively with tri-(n-butyl)tin hydride. In this manner it is possible to convert avermectin derivatives into the milbemycin series (q.v. Tetrahedrone Letters, Vol. 24, No. 48, pp. 5333–5336, 1983).

In the process of this invention, compounds of formula I are obtained by singulett oxygen oxidation from appropriately substituted milbemycin derivatives [X=—CH(OR₁)—] or 5-keto-milbemycin derivatives [X=—CO—] of the formula II

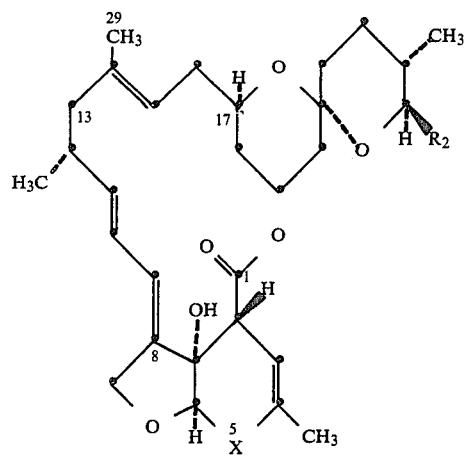

wherein X and R₂ are as defined for formula I, and subsequent selective reduction on the 15-peroxide and 14-peroxide obtained as intermediate

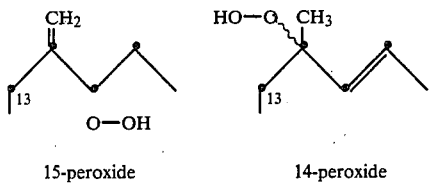

with sodium borohydride, lithium aluminium hydride or triphenylphosphine. The reaction is carried out in visible light in the presence of a sensitiser, under normal pressure and in the temperature range from −90° C. to +45° C., preferably from 0° to +20° C., in an inert solvent. It is preferred to carry out the reaction in an irradiating apparatus.

The reaction course can be illustrated as follows:
(1) oxygen+light+sensitiser
(2) reduction compounds of formula II→compounds I
(q.v. H. H. Wassermann et al, "Singulett Oxygen", Academic Press, New York 1979; or B. Ranby etz al., "Singulett Oxygen Reactions with Organic Compounds and Polymers", Wiley, New York 1978).

Examples of suitable solvents are ethers and ethereal compounds such as diethyl ether, diisopropyl ether, dioxan and tetrahydrofuran; aromatic hydrocarbons such as benzene, toluene and xylenes; ketones such as acetone, methyl ethyl ketone and cyclohexanone; nitriles such as acetonitrile; esters such as ethyl acetate and butyl acetate; and dimethylformamide, dimethylsulfoxide and halogenated hydrocarbons; or mixtures of these solvents with water.

Suitable sensitisers are dyes such as methylene blue, Bengal, pink, chlorophyll, erythrosin, eosine, zinc tetraphenyl porphine, hematoporphyrin, riboflavine, fluorescein or acridine orange. Selective reduction is carried out in the temperature range from 0° to 20° C., without further purification, after conclusion of the oxidation.

As light source it is convenient to use a lamp having a strength of 60 to 500 watt, preferably of 100 to 350 watt. If it is desired to protect the 5-hydroxy group, then suitable protective groups are the silyl and acyl groups mentioned for R or e.g. a benzyl ether, methoxyethoxymethyl ether, or dihydrofuran or dihydropyran radicals. These protective groups can be introduced into compounds of formula II and later removed again in conventional manner. Conventional acylation of the 5-OH group with the corresponding acyl halides or acyl anhydrides or by reaction of the 5-OH group with the appropriately substituted silane derivative of the formula

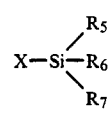

affords all those previously mentioned derivatives of the formula I or II in which R₁ has a meaning different from hydrogen, and R₅, R₆ and R₇ are as defined for formula I, with the term acyl halide signifying acyl chloride or acyl bromide and X being a silyl leaving group. Silyl leaving groups X comprise for example bromide, chloride, cyanide, azide, acetamide, trifluoroacetate, and trifluoromethanesulfonate. The above recitation constitutes no limitation, and other typical silyl leaving groups are known to the skilled person.

5-O-Acylations and 5-O-silylations are carried out in anhydrous medium, preferably in inert solvents and, most preferably, in aprotic solvents. The reaction conveniently takes place in the temperature range from 0° to 80° C., preferably from 10° to 40° C. It is preferred to add an organic base. Examples of suitable bases are tertiary amines such as triethylamine, triethylenediamine, triazole and, preferably, pyridine, imidazole or 1,8-diazabicyclo[5.4.0]-undec-7-ene (DBU).

The removal of these silyl and acyl radicals R₁ in the 5-position is effected by selective mild hydrolysis (→R=H) with e.g. an arylsulfonic acid in alcoholic solution, or by another method commonly known to the skilled person.

The compounds of formula II, wherein R₁ is hydrogen, are either known from U.S. Pat. No. 3,950,360 and were originally designated as "Antibiotics B-41-A", later called "milbemycin A compounds", or they are known from U.S. Pat. No. 4,346,171 and designated as "B-41D" or "milbemycin D"; or they are known from U.S. Pat. No. 4,173,571 and designated as 13-deoxy-22,23-dihydro-avermectin (R₂=sec-butyl). They have the structure

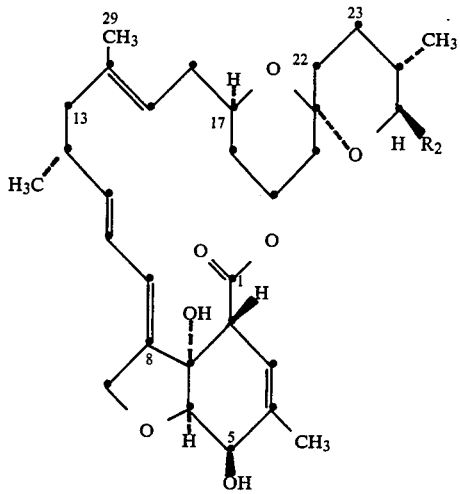

$R_2=CH_3$; milbemycin $A_3$
$R_2=C_2H_5$; milbemycin $A_4$
$R_2=isoC_3H_7$; milbemycin D
$R_2=sec-C_4H_9$;  13-deoxy-22,23-dihydro-C-076-B1a-aglycon, or 13-deoxy-22,23-dihydro-avermectin-B1a-aglycon.

The present invention further relates to pesticidal compositions for controlling ecto- and endoparasites as well as harmful insects, which compositions contain as at least one active ingredient a compound of the formula I, together with conventional carriers and/or dispersing agents.

The compounds of formula I are most suitable for controlling pests of animals and plants, including ectoparasites of animals. These last mentioned pests comprise those of the order Acarina, in particular pests of the families Ixodidae, Dermanyssidae, Sarcoptidae, Psoroptidae; of the orders Mallophaga, Siphonoptera, Anoplura (e.g. family of the Haematopinidae); and of the order Diptera, in particular pests of the families Muscidae, Calliphoridae, Oesterridae, Tabanidae, Hippoboscidae, and Gastrophilidae. The compounds of formula I can also be used against hygiene pests, especially of the order Diptera (families Sarcophigidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp. They also have excellent activity against sucking insects of the order Homoptera, in particular against pests of the families Aphididae, Delphacidae, Cicadellidae, Psyllidae, Loccidae, Diaspididae and Eriophyidae (e.g. the rust mite or citrus fruit); of the orders Hemiptera, Heteroptera and Thysanoptera; and against plant-destructive insects of the orders Lepidoptera, Coleoptera, Diptera and Orthoptera.

The compounds of formula I are also suitable for use against pests in the soil.

The compounds of formula I are therefore effective against all development stages of sucking and eating insects in crops such as cereals, cotton, rice, maize, soybeans, potatoes, vegetables, fruit, tabacco, hops, citrus fruit, avocados and others.

The compounds of formula I are also affective against plant nematodes of the species Meloidogyne, Heteroders, Pratylenchus, Ditylenchus, Radolphus, Rhizoglyphus and others.

Furthermore, the compounds of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Cappillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based endoparasiticides.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances, As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 50 mg/kg of body weight, and are applied to enclosed crop areas, to pens, livestock buildings or other buildings in amounts of 10 g to 1000 g per hectare.

The formulations, i.e. the compositions or preparations containing the compound (active ingredient) of the formula I are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contains a $C_8$–$C_{22}$ alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct or p-nonylphenol with 4 to 14 moles of ethylene oxide.

The surfactants customarily employed in the art of formulation are described e.g. in "McCutcheon's Detergents and Emulsifiers Annual", MC Publishing Corp. Ridgewood, N.J., 1982.

The pesticidal compositions usually contain 0.01 to 95%, preferably 0.1 to 80%, of a compound of the formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

The composition may also contain further ingredients, such as stabilisers, antifoams, viscosity regulators, binders, tackifiers as well as fertilisers or other active ingredients in order to obtain special effects.

The compounds of formula I are also versatile reactive compounds for obtaining further milbemycin derivatives.

EXAMPLE 1

Preparation of $\Delta^{14,29}$-15-hydroxymilbemycin D (formula Ia) and 14-hydroxy-$\Delta^{15,16}$-milbemycin D (formula Ib) from milbemycin D In a glass irradiation apparatus, a solution of 5.56 g of milbemycin D and 0.03 g of methylene blue in 400 ml of acetonitrile is irradiated, under a stream of oxygen, with visible light for 10 hours at a temperature of 20° C. (200 watt projector lamp). The reaction mixture is then reduced with 3.9 g of triphenylphosphine at 20° C. The reaction mixture is concentrated and the residue is chromatographed through a column of silica gel eluted with a 3:1 mixture of methylene chloride/ethyl acetate, affording 4.10 g of $\Delta^{14,29}$-5-hydroxy-milbemycin D with a melting point of 228°–229° C.; mass spectrum m/e: 572 (M+), 554. Also obtained is 0.34 g of 14-hydroxy-$\Delta^{15,16}$-milbemycin D with a melting point of 252°–254° C.; mass spectrum m/e: 572 (M+), 554.

EXAMPLE 2

Preparation of 5-keto-$\Delta^{14,29}$-15-hydroxy-milbemycin D (formula Ia) and 5-keto-14-hydroxy-$\Delta^{15,16}$-milbemycin D (formula Ib) from 5-keto-milbemycin D.

(a) Preparation of 5-keto-milbemycin D. A mixture of 1 g of milbemycin D, 2 g of activated manganese dioxide and 50 ml of anhydrous methylene chloride is stirred for 4 hous at 20°–25° C. The reaction mixture is filtered and the filtrate is purified over a short column (about 30 cm) of silicagel, affording 1 g of yellowish amorphous 5-keto-milbemycin with a melting point of 140°–150° C.

(b) The singulett oxidation of the 5-keto-milbemycin prepared in (a) and the further working up are effected by the method described in Example 1. After chromatography over silicagel there is obtained 0.6 g of 5-keto-$\Delta^{14,29}$-15-hydroxy-milbemycin D with a melting point of 160°–165° C.; mass spectrum m/e: 570 (M+), 552.

Also obtained are 30 mg of 5-keto-14-hydroxy-$\Delta^{15,16}$-milbemycin D with a melting point of 170°–174°–C.

EXAMPLE 3

Preparation of 5-keto-$\Delta^{14,29}$-15-hydroxy-milbemycin D (formula Ia) and 5-keto-14-hydroxy-$\Delta^{15,16}$-milbemycin D (formula Ib) for milbemycin D The oxidation with manganese dioxide as follow-up reaction of $\Delta^{14,29}$-15-hydroxymilbemycin D and 14-hydroxy-$\Delta^{15,16}$-milbemycin D obtained by the singulett oxygen oxidation of Example 1 affords, in quantitative yield, 5-keto-$\Delta^{14,29}$-15-hydroxy-milbemycin D and 5-keto-14-hydroxy-$\Delta^{15,16}$-milbemycin D respectively

EXAMPLE 4

Preparation of 5-acetyl-$\Delta^{14,29}$-15-hydroxy-milbemycin D and 5-acetyl-14-hydroxy-$\Delta^{15,16}$-milbemycin D from milbemycin D (a) Preparation of 5-acetyl-milbemycin D.

To 560 g (1.0 Mm) of milbemycin D in 20 ml of pyridine are added 160 mg (1.6 mM) of acetic anhydride and the mixture is stirred at room temperature overnight. The pyridine is evaporated off and the residue is taken up in 20 ml of ethyl acetate. The organic phase is shaken once with 10 ml of a 1N solution of hydrochloric acid and then with 10 ml of a saturated solution of $NaHCO_3$ and finally with 10 ml of a concentrated solution of NaCL. The organic phase is separated and dried over $Na_2SO_4$, filtered and concentrated by evaporation, affording 580 mg of 5-acetyl-milbemycin D as an amorphous, slightly yellow powder with a melting point of 115°–120° C.

The acyl derivatives, milbemycin $A_3$, milbemycin $A_4$ and the 13-desoxy-avermectin derivative ($R_2$=sec-butyl) can also be prepared in analogous manner.

(b) 560 mg of 5-acetyl-milbemycin D and 20 g of methylene blue in 40 ml of acetonitrile are treated with oxygen for 8 hours at 18°–22C. in an irradiation apparatus (200 watt projector lamp). The reaction mixture is then reduced with 40 mg of triphenylphosphine at room temperature. The reaction mixture is concentrated and the residue is chromatographed through a column of silica gel eluted with a 3:1 mixture of methylene chloride/ethyl acetate, affording 390 mg of 5-acetyl-$\Delta^{14,29}$-15-hydroxy-milbemycin D with a melting point of 153°–156° C.; mass spectrum m/e: 614 (M+), 596. Also obtained are 45 mg of 5-acetyl-14-hydroxy-$\Delta^{15,16}$-milbemycin D with a melting point of 151°–154° C.

EXAMPLE 5

Preparation of $\Delta^{14,29}$-15-hydroxy-milbemycin $A_4$ and 14-hydroxy-$\Delta^{15,16}$-milbemycin $A_4$ from milbemycin $A_4$ 540 mg (1 mM) of milbemycin $A_4$ in 100 ml of acetonitrile are oxidised with singulett oxygen in accordance with Example 1 and subsequently reduced with triphenylphosphine. Purification by flash chromatography through silica gel eluted with a 1:1 mixture of cyclohexane/ethyl acetate yields 310 mg of $\Delta^{14,29}$-15-hydroxymilbemycin $A_4$ with a melting point of 222°–225° C.; mass spectrum m/e: 558 (M+), 540. Also obtained are 40 mg of 14-hydroxy-$^{15,16}$-Milbemycin $A_4$ with a melting point of 147°–152° C.; mass spectrum m/e: 558 (M+), 540.

EXAMPLE 6

Preparation of 5-dimethyl-tert-butylsilyl-$\Delta^{14,29}$-15-hydroxy-milbemycin $A_3$ and 5-dimethyl-tert-butylsilyl-14-hydroxy-$\Delta^{14,15}$-milbemycin $A_3$ from milbemycin $A_3$ (a) Preparation of 5-dimethyl-tert-butylsilyl-milbemycin $A_3$.

A reaction vessel is charged at room temperature with 480 mg (7 mM) of imidazole and 460 mg (3 mM) of dimethyl tert-butylchlorosilane in 20 ml of methylene chloride. With stirring, a solution of 655 mg (1.2 mM) of milbemycin $A_3$ in 10 ml of methylene chloride is slowly added dropwise and the reaction mixture is heated overnight under reflux (40° C.). The reaction mixture is concentratd and the residue is purified over silica gel and dried, affording 730 mg of amorphous 5-dimethyl-tert-butylsilyl-milbemycin $A_3$ with a melting point of 55°–60° C.

Milbemycin $A_4$, milbemycin D and the 13-desoxyavemectin derivative ($R_2$=sec-butyl) can be silylated in the same manner. Methyldiphenyl chlorosilane or bis(isopropyl)methyl chlorosilane can also be used with advantage in this reaction.

(b) In accordance with the procedure described in Example 4b), 550 mg of 5-dimethyl-tert-butylsilyl-$\Delta^{14,29}$-15-hydroxy-milbemycin $A_3$ (m.p. 238°–240° C.; mass spectrum m/e: 658 (M+), 640) can be obtained from 720 mg of 5-dimethyl-tert-butylsilyl-mibemycin $A_3$ by singulett oxygen oxidation with Bengal pink as sensitiser, and subsequent reaction of the peroxides with triphenylphosphine.

Also obtained are 42 mg of amorphous 5-dimethyl-tert-butylsilyl-14-hydroxy-$\Delta^{15,16}$-milbemycin $A_3$ with a melting point of 45°–50° C.

EXAMPLE 7

Preparation of $\Delta^{14,29}$-15-hydroxy-milbemycin $A_3$ and 14-hydroxy-$\Delta^{15,16}$-milbemycin $A_3$ 120 mg of 5-dimethyl-tert-butylsilyl-$\Delta^{14,29}$-15-hydroxy-milbemycin $A_3$ and 2 ml of a 1% solution of p-toluenesulfonic acid in methanol are stirred for 9 hours at room temperature and then treated with a 5% aqueous solution of $NaHCO_3$. After extraction with three 2 ml portions of diethyl ether, the organic phase is concentrated by evaporation and the crude product is chromatographed over 20 g of silica gel eluted with a 1:12 mixture of acetone/methylene chloride, affording 67 mg of $\Delta^{14,29}$-15-hydroxy-milbemycin $A_3$ with a melting point of 219°–222° C.

In corresponding manner, 38 mg of 14-hydroxy$\Delta^{15,16}$-milbemycin $A_3$ (m.p. 128-°132°-C.) are obtained from 60 mg of 5-dimethyl-tert-butylsilyl-14-hydroxy-$\Delta^{15,16}$-milbemycin $A_3$.

Compounds of formula I can be prepared in accordance with the foregoing Examples. In the following Table: Ia=$\Delta^{14,29}$-15-ol derivative, Ib=14-hydroxy-$\Delta^{15,16}$ derivative.

If no particulars are given in the $R_1$ column, the compound in question is a 5-keto-milbemycin (X=CO). $^1$HNMR data were determined in $CDCL_3$ at 250 MHz, using $Si(CH_3)_4$ as reference.

| Compound | A | $R_1$ | $R_2$ | Physical data |
|---|---|---|---|---|
| 1.1 | Ia | —OH | isoC$_3$H$_7$ | m.p. 228–229° C. |
| 1.2 | Ib | —OH | " | m.p. 252–254° C. |
| 1.3 | Ia | —OSi(CH$_3$)$_2$t-C$_4$H$_9$ | " | m.p. 235–238° C. |
| 1.4 | Ib | " | " | m.p. 145–150° C. |
| 1.5 | Ia | —OSiCH$_3$(C$_6$H$_5$)$_2$ | " | |
| 1.6 | Ib | " | " | |
| 1.7 | Ia | —O—COCH$_3$ | " | m.p. 153–156° C. |
| 1.8 | Ib | —O—COCH$_3$ | " | m.p. 151–154° C. |
| 1.9 | Ia | —O—COC$_2$H$_5$ | " | m.p. 157–160° C. |
| 1.10 | Ib | —O—COC$_2$H$_5$ | " | m.p. 155–159° C. |
| 1.11 | Ia | — | " | m.p. 160–165° C. |
| 1.12 | Ib | — | " | m.p. 170–174° C. |
| 1.13 | Ia | —OSi(CH$_3$)$_3$ | " | |
| 1.14 | Ib | —OSi(CH$_3$)$_3$ | " | |
| 2.1 | Ia | —OH | C$_2$H$_5$ | m.p. 222–225° C. |
| 2.2 | Ib | —OH | " | m.p. 147–152° C. |
| 2.3 | Ia | —OSi(CH$_3$)$_2$t-C$_4$H$_9$ | " | amorphous |
| 2.4 | Ib | " | " | m.p. 58–62° C. |
| 2.5 | Ia | —O—SO$_2$CH$_3$ | " | |
| 2.6 | Ib | —O—SO$_2$CH$_3$ | " | |
| 2.7 | Ia | —O—COCH$_3$ | " | m.p. 158–161° C. |
| 2.8 | Ib | —O—COCH$_3$ | " | m.p. 156–160° C. |
| 2.9 | Ia | —O—COC(CH$_3$)$_3$ | " | |
| 2.10 | Ib | —O—COC(CH$_3$)$_3$ | " | |
| 2.11 | Ia | — | " | NMR:4.91(s); 5,24(s) (C$_{13}$ = CH$_2$) |
| 2.12 | Ib | — | " | amorphous |
| 3.1 | Ia | —OH | CH$_3$ | m.p. 220–223° C. |
| 3.2 | Ib | —OH | CH$_3$ | amorphous |
| 3.3 | Ia | —OSi(CH$_3$)$_2$t-C$_4$H$_9$ | CH$_3$ | m.p. 238–240° C. |
| 3.4 | Ib | " | CH$_3$ | m.p. 45–50° C. |
| 3.5 | Ia | —O—COCH$_3$ | CH$_3$ | |
| 3.6 | Ib | —O—COCH$_3$ | CH$_3$ | |
| 3.7 | Ia | —O—COC$_6$H$_5$ | CH$_3$ | |
| 3.8 | Ib | —O—COC$_6$H$_5$ | CH$_3$ | |
| 3.9 | Ia | —O—SO$_2$C$_6$H$_5$ | CH$_3$ | amorphous |
| 3.10 | Ib | —O—SO$_2$C$_6$H$_5$ | CH$_3$ | |
| 3.11 | Ia | — | CH$_3$ | m.p. 145–148° C. |
| 3.12 | Ib | — | CH$_3$ | m.p. 152–156° C. |
| 4.1 | Ia | —OH | sec-C$_4$H$_9$ | NMR:4.92(s); 5.25(s)(C$_{13}$ = CH$_2$) |
| 4.2 | Ib | —OH | sec-C$_4$H$_9$ | |
| 4.3 | Ia | — | sec-C$_4$H$_9$ | NMR:4.91(s); 5.25(s)(C$_{13}$ = CH$_2$) |
| 4.4 | Ib | — | sec-C$_4$H$_9$ | |

FORMULATION EXAMPLES FOR ACTIVE INGREDIENTS OF THE FORMULA I (throughout, percentages are by weight)

| Wettable powders | (a) | (b) | (c) |
|---|---|---|---|
| compound of formula I | 25% | 50% | 75% |
| sodium lignosulfonate | 5% | 5% | — |
| sodium laurylsulfate | 3% | 5% | — |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| compound of formula I | 10% |
| octylphenol polyethylene glycol ether (4–5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| compound of formula I | 5% | 8% |
| talcum | 95% | — |
| kaolin | — | 92% |

Ready for use dusts are obtained by mixing the active ingredient with the carriers, and grinding the mixture in a suitable mill.

| Extruder granulate | |
|---|---|
| compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
|---|---|
| compound of formula I | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| Suspension concentrate | |
|---|---|
| compound of formula I | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

If the compounds of formula I, or compositions containing them, are used for controlling endoparasitic nematodes in domestic animals ands productive livestock, for example cattle, sheep, goats, horses, pigs, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I, or compositions containing them, can also be injected into animals, for example subcutaneously or by intraruminal injection, or applied to the bodies of the animals by the pour-or method. Administration by means of salt licks or molasses blocks is also possible.

BIOLOGICAL EXAMPLES

B1: Insecticidal stomach poison action against Spodoptera littoralis

Cotton plants are sprayed with a solution which contains 3, 12.5 or 50 ppm of the test compound. After the spray coating has dried, the plants are populated with larvae ($L_1$ stage) of Spodoptera littoralis. Two plants are used for each test compound and test species. The test is carried out at about 24°–C. and 60% relative humidity. Evaluations and intermediate evaluations are made about 24, 48 and 72 hours. At concentrations of 12.5 ppm, compounds 1.1, 1.2, 1.7, 1.11, 1.12, 1.13, 2.1, 2.2, 2.5, 2.7, 2.11, 2.12, 3.1, 3.2, 3.11, 4.1 and 4.3 effect complete kill after 24 hours.

B2: Action against plant destructive acarids: OP-sensitive Tetranychus urticae 16 hours before the start of the test, the primary leaves of bean plants (Phaseolus vulgaris) are infected with an infested piece of leaf from a mass culture of Tetranychus urticae. Upon removal of the piece of leaf, the artificially infected plants are sprayed to drip point with a solution containing 0.4 ppm or 1.6 ppm of the test compound. The temperature in the greenhouse compartment is about 25° C. A count of living and dead imagines and larvae is made under a stereoscopic microscope after 1 day and after 8 days. Compounds 1.1, 1.2, 1.3, 1.4, 1.7, 1.8, 1.9, 1.11, 1.12, 2.1, 2.2, 2.3, 2.7, 2.11, 2.12, 3.1, 3.2, 3.3, 3.4, 3.11, 3.12, 4.1 and 4.3 effect complete kill at a concentration of 1.6 ppm after 24 hours.

B3: Action against L₁ larvae of Lucilia sericata 1 ml of an aqueous suspension of test compound is mixed with 3 ml of a special larval culture medium at about 50° C. such that a homogeneous composition containing 250 ppm or 125 ppm is obtained. About 30 Lucilia sericata larvae (L₁) are put into each test tube containing active ingredient. A mortality count is made after 4 days. Compounds 1.1, 1.2, 1.11, 1.12, 2.1, 2.2, 2.3, 2.7, 2.11, 3.1, 3.2, 4.1 and 4.3 effect 100% kill at a concentration of 250 ppm.

B4: Acaricidal action against Boophilus microplus (Biarra strain)

Adhesive tape is applied vertically across a PVC plate so that 10 fully replete female Boophilus microplus ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.1 or 0.01 μg per tick is dissolved. Control ticks are injected with liquid containing no test compound. After this treatment, the ticks are detached from the support and kept in an insectarium at about 28° C. and 80% relative humidity until oviposition has taken place and the larvae have hatched from the eggs of the control ticks. The activity of the test compound is determined with the IR₉₀, i.e. the effective dose is determined at which 9 out of 10 female ticks (90%) even after 30 days lay eggs from which larvae are unable to hatch. Compounds 1.1, 1.2, 1.3, 1.7, 1.9, 1.10, 1.11, 1.12, 2.1, 2.2, 2.3, 2.7, 2.11, 2.12, 3.1, 3.2, 3.3, 3.4, 3.9, 4.1, 4.2 and 4.3 effected an IR₉₀ of 0.1 μg.

B5: Trial with sheep infected with nematodes (Haemonchus concortus and Trichostrongylus colubriformis)

The test compound is administered in the form of a suspension with a stomach probe or by intraruminal injection to sheep which have been artifically infected with Haemonchus concortus and Trichostrongylus. One to three animals are used for each dose. Each sheep is treated only once with a single dose, namely with 1 mg or 2 mg/kg of body weight. Evaluation is made by comparing the number of worm eggs excreted in the faeces of the sheep before and after treatment. Untreated sheep infected simultaneously and in the same manner are used as controls. In comparison with untreated and infected control groups, nematode infestation is reduced by 90 to 100% in sheep which have been treated with one of compounds 1.1–1.4, 1.7–1.12, 2.1–2.4, 2.7, 2.8, 2.11, 2.12, 3.1–3.4, 3.11, 3.12, 4.1 and 4.3 at 2 mg/kg.

What is claimed is:

1. A milbemycin derivative of the formula

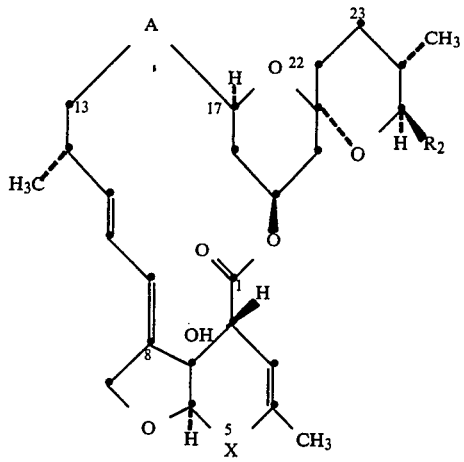

wherein

A is —C(=CH₂)—CH(OH)—CH₂— or —C(OH)(CH₃)—CH=CH—,

X is —CO— or —CH(OR₁)— wherein R₁ is hydrogen, $C_1$-$C_6$-alkyl-CO—, halo-$C_1$-$C_6$-alkyl-CO, phenyl-CO—, $C_1$-$C_4$-alkyl-phenyl-CO—, halophenyl-CO—, $C_1$-$C_4$-alkyl-SO₂—, phenyl-SO₂—, CH₃-phenyl-SO₂—, chloro-phenyl-SO₂—, nitrophenyl-SO₂—, or —Si(R₅)(R₆)(R₇) wherein R₅ is a $C_1$-$C_4$ aliphatic radical or benzyl, and R₆ and R₇ are each, independently of the other, a $C_1$-$C_4$ aliphatic radical, benzyl or phenyl, and;

R₂ is methyl, ethyl, isopropyl or sec-butyl.

2. A compound of claim 1, wherein R₁ is hydrogen and R₂ is isopropyl.

3. A compound of claim 1, wherein A is —C(=CH₂)—CH(OH)—CH₂—.

4. A compound of claim 3, wherein X is either —CO— or —CHOR₁—where R₁ is hydrogen.

5. A compound of claim 3, wherein R₁ is Si(R₅)(R₆)(R₇) in which R₅ is methyl, ethyl, propyl, isopropyl, or tert-butyl, and each of R₆ and R₇ is independently methyl, ethyl, isopropyl, tert-butyl, phenyl or benzyl, and R₂ is methyl, ethyl, isopropyl or sec-butyl.

6. A pesticidal composition which contains at least one compound of the formula

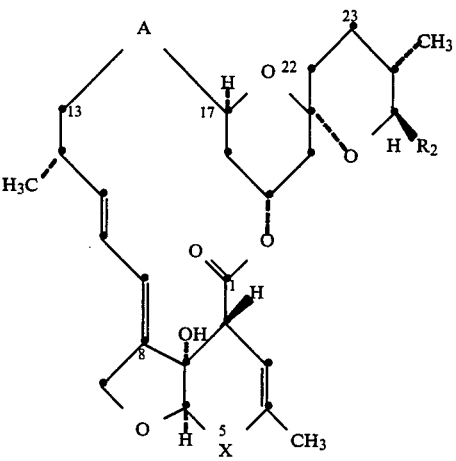

wherein

A is —C(=CH$_2$)—CH(OH)—CH$_2$— or —C(OH)(CH$_3$)—CH=CH—,

X is —CO— or —CH(OR$_1$)—wherein R$_1$ is hydrogen, C$_1$–C$_6$-alkyl-CO—, halo-C$_1$–C$_6$-alkyl-CO, phenyl-CO—, C$_1$–C$_4$-alkyl-phenyl-CO—, halophenyl-CO—, C$_1$–C$_4$-alkyl-SO$_2$—, phenyl-SO$_2$—, CH$_3$-phenyl-SO$_2$—, chloro-phenyl-SO$_2$—, nitrophenyl-SO$_2$—, or -Si(R$_5$)(R$_6$)(R$_7$) wherein R$_5$ is a C$_1$–C$_4$ aliphatic radical or benzyl, and R$_6$ and R$_7$ are each, independently of the other, a C$_1$–C$_4$ aliphatic radical, benzyl or phenyl, and;

R$_2$ is methyl, ethyl, isopropyl or sec-butyl, in an effective amount together with a suitable inert carrier.

7. A method of controlling ecto- and endoparasites of plants and animals, which comprises applying to said plants and animals a pesticidally effective amount of a compound of the formula

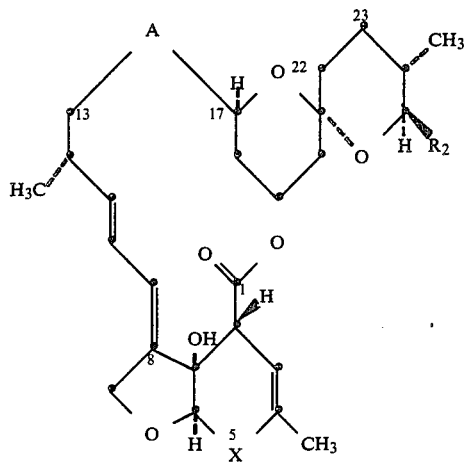

wherein

A is —C(=CH$_2$)—CH(OH)—CH$_2$— or —C(OH)(CH$_3$)-CH=CH—,

X is —CO— or —CH(OR$_1$)— wherein R$_1$ is hydrogen, C$_1$–C$_6$-alkyl-CO—, halo-C$_1$–C$_6$-alkyl-CO, phenyl-CO—, C$_1$–C$_4$-alkyl-phenyl-CO—, halophenyl-CO—, C$_1$–C$_4$-alkyl-SO$_2$—, phenyl-SO-$_2$—, CH$_3$-phenyl-SO$_2$—, chloro-phenyl-SO$_2$—, nitrophenyl-SO$_2$—, or —Si(R$_5$)(R$_6$)(R$_7$) wherein R$_5$ is a C$_1$ –C$_4$ aliphatic radical or benzyl, and R$_6$ and R$_7$ are each, independently of the other, a C$_1$–C$_4$ aliphatic radical, benzyl or phenyl, and.

R$_2$ is methyl, ethyl, isopropyl or sec-butyl.

* * * * *